US00PP37376P3

(12) United States Plant Patent
Cruz et al.

(10) Patent No.: US PP37,376 P3
(45) Date of Patent: Apr. 21, 2026

(54) GUAYULE PLANT NAMED 'E-B2WN-13167'

(50) Latin Name: *Parthenium argentatum*
Varietal Denomination: E-B2WN-13167

(71) Applicant: Bridgestone Corporation, Chuo-ku (JP)

(72) Inventors: Von Mark Vicente Cruz, Casa Grande, AZ (US); David Allen Dierig, Phoenix, AZ (US)

(73) Assignee: Bridgestone Corporation, Chuo-ku (JP)

( * ) Notice: Subject to any disclaimer, the term of this patent is extended or adjusted under 35 U.S.C. 154(b) by 0 days.

(21) Appl. No.: 19/187,105

(22) Filed: Apr. 23, 2025

(65) Prior Publication Data

US 2025/0331435 P1 Oct. 23, 2025

Related U.S. Application Data

(60) Provisional application No. 63/637,778, filed on Apr. 23, 2024.

(51) Int. Cl.
*A01H 5/12* (2018.01)
*A01H 5/02* (2018.01)
*A01H 6/00* (2018.01)

(52) U.S. Cl.
USPC ..... Plt./258
CPC ..... *A01H 6/00* (2018.05); *A01H 5/02* (2013.01); *A01H 5/12* (2013.01)

(58) Field of Classification Search
USPC ..... Plt./226, 263.1, 258
CPC ... A01H 5/12; A01H 5/04; A01H 5/00; A01H 6/14
See application file for complete search history.

(56) References Cited

PUBLICATIONS

Hammond et al. Research on Guayule, Technical Bulletin No. 1327, Agricultural Research Service United States Department of Agriculture, 1965, 5 introductory pages, pp. 1-11, 78-93. (Year: 1965).*

* cited by examiner

*Primary Examiner* — June Hwu
(74) *Attorney, Agent, or Firm* — Meredith E. Hooker; Stephanie M. Williams

(57) ABSTRACT

A new and distinct cultivar of *Parthenium argentatum* named E-B2WN-13167 is disclosed, characterized by reduced internode lengths, shorter leaf peduncles, thicker leaves, lower number of flowers, aborted seed production, and slower growth.

2 Drawing Sheets

Genus and species: *Parthenium argentatum.*
Variety denomination: 'E-B2WN-13167'.

BACKGROUND OF THE NEW PLANT

The present invention relates to a new and distinct variety of guayule, botanically known as *Parthenium argentatum* and hereinafter referred to by the variety name 'E-B2WN-13167' 'E-B2WN-13167' originated from controlled irradiation of seeds from the *Parthenium argentatum* USDA germplasm line AZ-2 (PI 599675), unpatented.

In 2016, a bulk seed lot of germplasm from AZ-2 was subjected to fast neutron irradiation. The seeds were sown and plants were grown for evaluation in Applicant's research facility located in Eloy, Arizona in USDA Plant Hardiness Zone 9b. Asexual reproduction of 'E-B2WN-13167' was performed by the propagation of vegetative cuttings at Applicant's research facility located in Eloy, Arizona. Multiple generations have since been produced and have shown that the unique features of this cultivar are stable and reproduced true-to-type in successive generations.

SUMMARY

The following characteristics of the new cultivar have been repeatedly observed and can be used to distinguish 'E-B2WN-13167' as a new and distinct cultivar of *Parthenium argentatum* plant.

The 'E-B2WN-13167' cultivar has not been observed and evaluated under all possible conditions and phenotypic differences may be observed with variations in environmental, climatic, and cultural conditions, however, without any variance in genotype.

Plants of the 'E-B2WN-13167' cultivar can be distinguished from the AZ-2 variety in several characteristics. For example, plants of the 'E-B2WN-13167' cultivar have reduced internode lengths, shorter peduncles, thicker leaves, lower numbers of flowers, and exhibit slower growth compared with the AZ-2. The 'E-B2WN-13167' cultivar has aborted seed production compared with the AZ-2 variety.

BRIEF DESCRIPTION OF THE DRAWINGS

The accompanying color photographs illustrate the overall appearance of 'E-B2WN-13167' showing the distinguishing characteristics as true as is reasonably possible to obtain in color reproductions of this type.

DETAILED BOTANICAL DESCRIPTION OF THE PLANT

Figure 1:
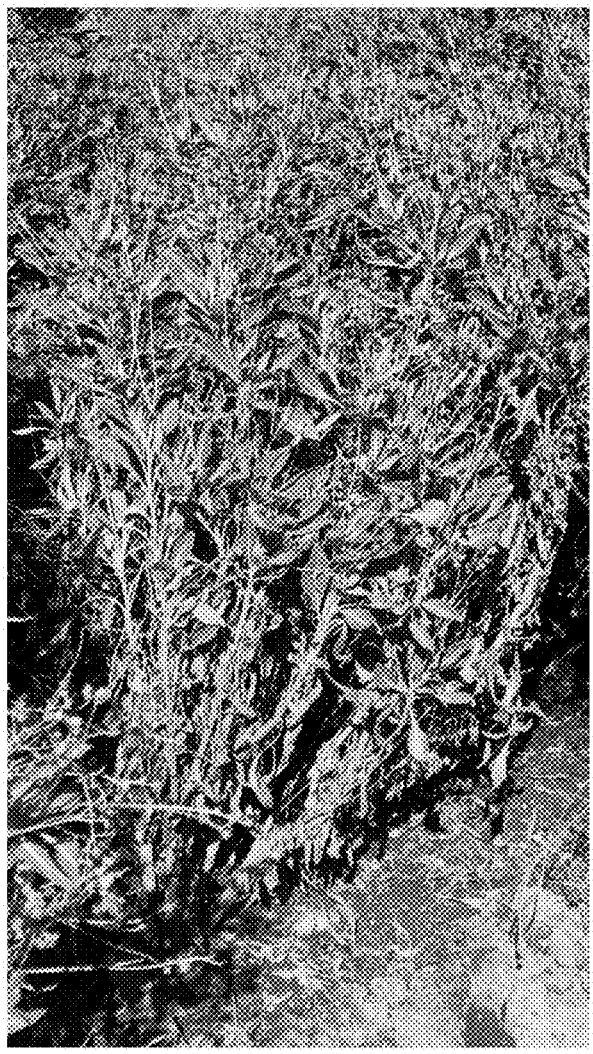
FIG. 1 is a photograph depicting the overall growth habit of the 'E-B2WN-13167' cultivar at the mature growth stage, wherein the leaves have transitioned to a mature greyish-green, described in greater detail herein.
Figure 2:
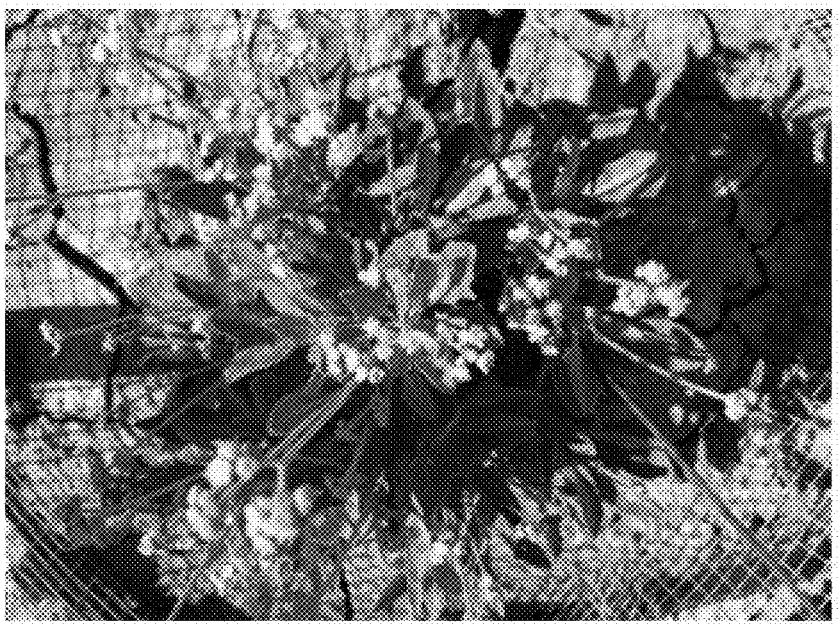
FIG. 2 is a photograph depicting the smaller flowers of the 'E-B2WN-13167' cultivar, showing leaves with a brighter color indicative of regrowth after harvest.
Figure 3:
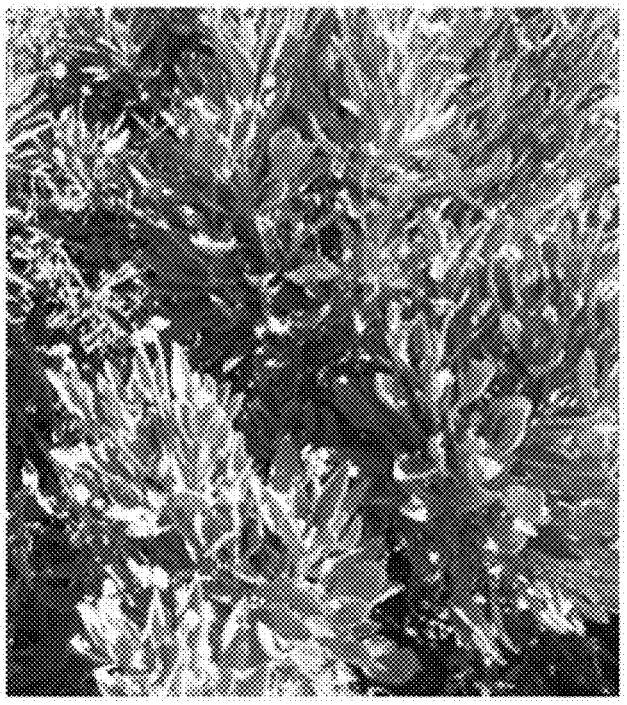
FIG. 3 is a photograph depicting the leaves of the 'E-B2WN-13167' cultivar, the mature growth stage, wherein the leaves have transitioned to a mature greyish-green, described in greater detail herein.

The following is a detailed botanical description of the 'E-B2WN-13167' cultivar. Observations, measurements, values, and comparisons were collected at Applicant's research facility in Eloy, Arizona, in USDA Plant Hardiness Zone 9b. Color references are to the Munsell Plant Tissue Color Charts. As can be observed from the provided figure, guayule leaves are rarely one solid color, but encompass hues, shades, tints, and color patterns.

The 'E-B2WN-13167' cultivar has shorter internodes resulting in higher numbers of leaves (37±3) per 10 cm branch section compared with AZ-2 (23±2). The internode length of the 'E-B2WN-13167' cultivar has a length of 0.6±0.23 cm on branches with 0.40 cm branch diameter and 0.72±0.26 cm on branches with 0.70 cm branch diameter, compared with the AZ-2 having an internode length of 0.70±0.25 cm on branches with 0.40 cm diameter and 1.27±0.45 cm on branches with 0.70 cm diameter.

The inflorescence of the 'E-B2WN-13167' cultivar have relatively short peduncles (5.01±1.66 cm) compared to other AZ-2 shrubs of the same age (17.62±3.68 cm). The 'E-B2WN-13167' cultivar had fewer flowers during the growing period, with a smaller flower diameter (0.65±0.02 cm) compared to the wild type (0.82±0.02 cm). The 'E-B2WN-13167' cultivar has a smaller leaf area (5.07±0.35 $cm^2$) compared to the AZ-2 (5.56±0.73 $cm^2$). The 'E-B2WN-13167' cultivar is smaller than the AZ-2, with the 'E-B2WN-13167' cultivar having a height of 55 cm and a width of 28 cm at two years, compared with the AZ-2 variety having a height of 105 cm and width of 96 cm at two years. In addition, the 'E-B2WN-13167' cultivar shows a slower rate of growth (0.06 cm/day) compared to the AZ-2 variety (0.1 cm/day). The 'E-B2WN-13167' cultivar has a relatively higher amount of rubber and lower biomass compared with the AZ-2 variety in the tested environment.

Botanical classification:
- i. *Family*.—Asteraceae.
- ii. *Genus*.—*Parthenium*.
- iii. *Species*.—*Argentatum*.
- iv. *Common name*.—Guayule.
- v. *Duration*.—Perennial.

Parentage: i. Controlled irradiation of seeds from the *Parthenium argentatum* USDA germplasm line AZ-2 (PI 599675), unpatented.

Propagation:
- i. *Type*.—Vegetative cuttings.
- ii. *Success of rooting*.—Approximately 20% under standard soil cutting propagation practices.
- iii. *Rooting system*.—Deep, coarse taproot and a shallow fibrous system.
- iv. *Seeds*.—No viable seed observed. Low seed production.
- v. *Temperature to develop roots*.—10° C. –35° C.

Plant characteristics:
- i. *Height*.—55 cm at 2 years, 70 cm at 4 years.
- ii. *Width*.—28 cm at 2 years, 50 cm at 4 years.
- iii. *Commercial crop time*.—2 years.
- iv. *Growth habit*.—Shrub with thick lignified stems, and a low, spreading form.
- v. *Growth rate*.—0.06 cm/day.
- vi. *Internode length*.—0.65±0.23 cm on 0.40 cm branch diameter 0.72±0.26 cm on 0.70 cm branch diameter.

Stems/branches:
- i. *Quantity*.—fewer branches compared to wild type AZ-2.
- ii. *Surface texture*.—Mature: bark with shallow fissures and striations.
- iii. *Color*.—7.5GY 7/2 (Munsell color chart) at younger growth stage becoming striated with bark color 7.5YR 4/4 and 2.5Y 6/2.

Foliage description:
- i. *Quantity of leaves*.—37±3 per 10 cm section of branch.
- ii. *Type of leaves*.—Densely haired leaves covered with white wax on upper and lower surfaces.
- iii. *Leaf shape*.—Lanceolate to oblanceolate, including oblong. Apex is either pointed or rounded; base tapers to the petiole.
- iv. *Margin*.—Serrated, entire or with a few scattered teeth or shallow lobes.
- v. *Length of leaf*.—3.46±1.2 cm.
- vi. *Width of leaf*.—0.78±0.2 cm.
- vii. *Leaf area*.—5.07±0.35 $cm^2$.
- viii. *Color*.—1. Mature leaves: Continuous gradient from 7.5GY 5/2 to 7.5GY 6/2 (Munsell color chart). 2. Leaves from newly regenerated plant: 7.5GY 4/2 or 7.5GY 5/4.
- ix. *Arrangement*.—Alternate.
- x. *Texture*.—wooly, silvery hairs on upper and lower surfaces.

Flowering:
- i. *Flowering habit*.—Indeterminate.
- ii. *General inflorescence*.—1. Flower diameter: 0.65±0.02 cm. 2. Color: White petals N10. 3. Type: Composite. 4. Arrangement: composite, fewer heads compared to wild type AZ-2. 5. Shape: Radiate. 6. Ray floret: a. Number per inflorescence head: 5. 7. Disc Floret: a. Average number per inflorescence: 10-15.
- iii. *Peduncle*.—1. Length: 5.01±1.66 cm. 2. Color: Varying, with some 5Y 7/2 and some at 2.5GY 7/2.

Use: Commercial production of natural rubber, ethanol, non-toxic adhesives, and hypoallergenic latex.

Rubber production: Rubber content after two years was 3.58% relative to biomass.

Fecundity:
- i. *Seed production*.—No viable seeds.

Disease and pest resistance: Resistant to many pests and diseases due to production of terpene resins. Disease and insect resistance is typical of the species, thus no claims are made of any superior disease or insect resistance with this cultivar. The species generally show resistance to aphids, mites, whiteflies, thrips, leaf beetles, and termites.

What is claimed is:

1. A new and distinct cultivar of *Parthenium argentatum* plant named 'E-B2WN-13167', substantially as described and illustrated herein.

* * * * *